United States Patent [19]

Nelson

[11] 4,453,017

[45] Jun. 5, 1984

[54] PROCESS FOR THE METHYLATION OF PHENOLIC COMPOUNDS WITH TRIMETHYL PHOSPHATE

[75] Inventor: Randall B. Nelson, Shelton, Wash.

[73] Assignee: International Telephone and Telegraph Corporation, New York, N.Y.

[21] Appl. No.: 364,326

[22] Filed: Apr. 1, 1982

[51] Int. Cl.$^3$ .................. C07C 41/16; C07C 45/61
[52] U.S. Cl. .................................. 568/433; 562/475; 564/223; 568/312; 568/630; 568/648; 568/655
[58] Field of Search .............. 568/433, 648, 312, 630, 568/655; 562/475; 564/223

[56] References Cited

PUBLICATIONS

Noller et al., J.A.C.S., vol. 55, (1933), 424–425.
Toy, J.A.C.S., vol. 66, (1944), 499.

*Primary Examiner*—Bernard Helfin
*Attorney, Agent, or Firm*—James B. Raden; Harold J. Holt

[57] ABSTRACT

A methylated phenolic ether is prepared by reacting in the absence of a protic solvent a phenolic compound containing an unreacted phenolic hydroxy group with trimethyl phosphate, the reaction occurring in one step and without the intermediate preparation of a phenolate.

7 Claims, No Drawings

PROCESS FOR THE METHYLATION OF PHENOLIC COMPOUNDS WITH TRIMETHYL PHOSPHATE

This invention relates to a process for the preparation of a methylated phenolic ether from the corresponding phenolic compound.

It is well known that phenols, particularly lignin derived phenols, may be generally alkylated by the use of alkyl sulfates, alkyl halides or alkyl sulfonates. A typical example of such a reaction is shown in *Organic Syntheses,* Collective Vol. II, page 619, 1943, in which veratraldehyde is prepared from vanillin, a lignin derived chemical. The process there shown is a two-step reaction involving the preparation of an intermediate sodium salt or phenolate with an alkali hydroxide, or other strong base, and water as a solvent and the subsequent alkylation of the phenolate with dimethyl sulfate to produce the alkylated phenol. This process is similar to those employed in the chemical industry for the production of veratraldehyde from vanillin.

These processes are hazardous in that the alkyl sulfates, alkyl halides, and alkyl sulfonates are toxic and present exposure problems due to their volatility. Less hazardous alkylating agents are known but they have not been commercially used because they tend to hydrolyze during the alkylation reaction resulting in relatively poor yields. One such reaction is shown, for example, in W. Voss and E. Blanke, *Ann. der Chemie,* 485, 258 (1931) where an alkyl sulfite is used for the conversion of phenol to anisole by the two-step sodium phenolate reaction. Alkyl sulfites have also been disclosed as useful in the O-alkylation of stabilized enolates. See, for example, Y. Hara and M. Matsuda, *Bull. Chem. Soc. (Japan),* Vol. 49, 1126 (1976).

Another known class of less hazardous alkylating agents are the alkyl phosphates. They have been disclosed as capable of alkylating phenols. See, for example C. R. Noller and G. R. Dutton, *J. Am. Chem. Soc.,* vol. 55, 424 (1933). However, because of relatively low yields as compared with the alkyl sulfates, the phosphates have not been used for phenolic alkylation reactions. Trialkyl phosphates have also been disclosed as alkylating agents for alcohols—A.D.F. Toy, *J. Am. Chem. Soc.,* Vol. 66, 499 (1944) and for heterocyclic amines—K. Yamauchi and M. Kinoshita, *J.C.S. Perkin I,* 391 (1973). However, both alcohols and amines are strong nucleophilic compounds whereas phenolic compounds are non-nucleophilic or weakly nucleophilic and thus present special alkylation difficulties.

It is a primary object of the present invention to provide an effective process for the production of phenolic ethers by the alkylation of phenols which does not require the use of hazardous alkylating agents.

It is an additional object of the invention to provide such an alkylation process which is relatively simple and involves mild reaction conditions.

The foregoing and other objects of the invention are achieved in a process for the preparation of a methylated phenolic ether which comprises reacting in the absence of a protic solvent a phenolic compound containing an unreacted phenolic hydroxy group with trimethyl phosphate until an methylated phenol is produced, the reaction occuring in one step and without the intermediate production of a phenolate.

The present process may be carried out as a melt phase reaction in the absence of a solvent or, alternatively, may be carried out in the presence of an aprotic solvent, preferably a dipolar aprotic solvent, together with a weak base. The melt phase methylation reaction is carried out at a temperature of at least the melting point of the phenol, preferably in the presence of a small amount of a base catalyst. The melt phase reaction is the subject of my copending application Ser. No. 364,325, filed of even date herewith. Further and more detailed description of the melt phase reaction may be obtained from the foregoing copending application, the disclosure of which is hereby incorporated by reference. If the methylation reaction is carried out in the presence of an aprotic solvent, from 0.1 to 10 mol percent of a weak base such as a carbonate salt should be used. The carbonate salt may, for example, be sodium, potassium, magnesium or calcium carbonate.

The present process avoids the prior formation of a phenolate and it is carried out in the absence of a protic solvent. Two step phenolic alkylation via the phenolate reaction requires the presence of a protic solvent or at least a protic component in the solvent. Prior phenolic alkylation reactions either introduced a protic solvent, such as water, at the start of the reaction, or insured the formation of a protic solvent during the course of the reaction by the addition of a strong base. In the present process, the reaction is carried out in the melt phase and no solvent is used or, alternatively, the reaction is carried out under anhydrous conditions in the presence of an aprotic solvent. If an aprotic solvent is used, it is used in conjunction with a weak base so that a protic solvent is not formed during the alkylation reaction. For the same reasons, the reaction is carried out under anhydrous conditions to avoid the presence of water, a protic solvent. Suitable dipolar aprotic solvents which may be used in the practice of the invention are dimethylformamide, dimethylacetamide, dimethylsulfoxide and sulfolane.

The starting phenolic compound will normally be a lignin derived mono- or polycyclic phenol. The reaction may generally be represented by the following equation showing the conversion of the phenolic compound into the corresponding ether:

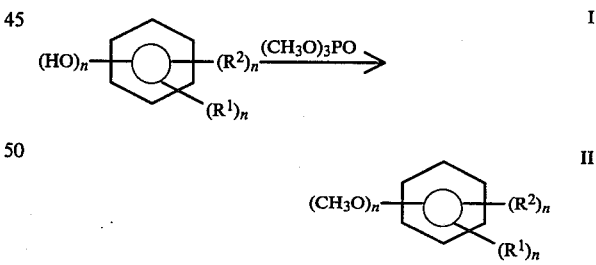

In the formulae above, $R^1$ and $R^2$ may be the same or different and are a radical selected from the group consisting of H, OH, alkyl, alkenyl, cycloalkyl, alkoxy, aryl, halogen and a carbonyl radical such as an aldehyde, ketone, ester, amide and acid, at least one of $R^1$ and $R^2$ preferably being —$COR^3$ where $R^3$ is hydrogen, an alkyl, cycloalkyl or aryl radical. n is from one to four. Where $R^1$ or $R^2$ is aryl, it may be attached to a single carbon atom of the phenolic nucleus (to form a biphenyl, for example) or it may share two carbon atoms to form a polycyclic phenol (as for example, naphthalene compounds). The orientation of the radicals may be varied in the ortho, meta or para position with respect to the —OH group and with respect to each other.

The alkylating agent need not be added in excess, however an excess is preferable. In the final methylated product, the —OH group, or groups, are substituted with the methyl moiety of the methylating agent to become the corresponding ether of the starting compound.

Examples of phenolic compounds falling within the above formula I are such monohydric phenols as phenol and o-, m- and p-cresol and guaiacol; phenolic aldehydes such as protocatechualdehyde, vanillin, syringaldehyde, p-hydroxybenzaldehyde and 5-formylvanillin; phenolic ketones such as p-hydroxyacetophenone, acetovanillone, acetosyringone, acetamidophenol; and phenolic acids such as vanillic acid, syringic acid and p-hydroxybenzoic acid. The preferred phenolic reactants are those having at least one carbonyl functionality.

A key advantage of the present process is the substantially greater level of safety of the trimethyl phosphate methylating agents as compared with traditional alkylating agents. All alkylating agents are potentially hazardous, but the degree of severity of trimethyl phosphate is substantially less than that of the sulfates, halides or sulfonates.

In a preferred embodiment of the process of the invention utilizing the melt phase reaction, a lignin derived phenol is melted and contacted with an anhydrous alkali carbonate and two to three molar excess of trimethyl phosphate under at least atmospheric pressure. Alternatively, the carbonate may be added before melting is initiated. The trimethyl phosphate is added progressively, i.e., incrementally as the reaction progresses, so as to keep the reaction temperature near the initial feed temperature, i.e., about 5° to 10° C. above the melting point of the phenol, until a slight stoichiometric excess (the preferred amount is usually about 1.2 molar equivalent of alkylating agent relative to phenol) of alkylating agent has been added. After addition of methylating agent, the temperature is maintained for a brief period (i.e., several hours) to insure completion of reaction and then the mixture is cooled to a moderate (e.g., 50° C.) temperature and drowned in water. Total reaction time is normally from 1 to 10 hours. The product can be collected directly or, if an oil, can be extracted into a suitable organic solvent and recovered in a manner familiar to those skilled in the art. Alternatively, the oil itself may be separated from the drowned reaction mixture and purified by one of several known standard methods such as fractional distillation. For many purposes, however, the crude product is of sufficient purity (often 95% assay) for use directly in the intended product.

In a preferred embodiment of the process of the invention utilizing a dipolar aprotic solvent, a lignin derived phenol is dissolved in the anhydrous solvent and contacted with an anhydrous alkali carbonate and two to three molar excess of the trimethyl phosphate under at least atmospheric pressure. Alternatively, the carbonate may be added before dissolution is initiated. The mixture is heated to near 100° C. (or other suitable temperature). The trimethyl phosphate is added progressively, i.e., incrementally as the reaction progresses, so as to keep the reaction temperature near the initial feed temperature, until a slight stoichiometric excess (the preferred amount is usually about 1.2 molar equivalents of alkylating agent realtive to phenol) of alkylating agent has been added. After addition of methylating agent, the temperature is maintained for a brief period (i.e., from one to several hours) to insure completion of reaction and then the mixture is cooled to a moderate (e.g., 50° C.) temperature and drowned in water. Total reaction time is normally from 1 to 10 hours. The product can be collected, extracted and recovered as set forth above for the melt phase reaction.

The following examples illustrate the practice of the invention. Unless otherwise indicated, all parts and percentages are by weight.

EXAMPLE 1

This example illustrates the preparation of veratraldehyde from vanillin.

In a three-neck flask (capacity 100 ml) equipped with a mechanical stirrer and reflux condenser, 5.00 g (0.033 mol) of vanillin and 5.00 g (0.036 mol) of anhydrous potassium carbonate were placed and the mixture was heated under a nitrogen atmosphere to 85° C. The mixture was a clear to amber melt of vanillin with carbonate in suspension. To this mixture was added 5.00 ml (0.043 mol) of trimethyl phosphate over about 5 minutes while maintaining the reaction temperature below 125° C. The mixture was maintained at about 80° C. for one hour and then cooled to 40° C. The mixture was poured into 20 ml water and extracted two times with 20 ml of methylene chloride. The combined extracts were dried over anhydrous potassium carbonate, filtered, and concentrated to give 5.4 g (99%) of veratraldehyde as a pale oil.

EXAMPLE 2

This example also illustrates the preparation of veratraldehyde from vanillin.

In an apparatus similar to Example 1, 15.0 g (0.099 mol) of vanillin and 10.0 g (0.072 mol) of anhydrous potassium carbonate were heated under nitrogen to 90° C. To this clear slurry was added over about 10 minutes 13.5 ml (0.112 mol) of trimethyl phosphate while holding the temperature below 110° C. The mixture was stirred and heated to 65°-75° C. for three hours then cooled to 35° C. and quenched with 80 ml of water to precipitate an oil. On stirring a light powder precipitated which was filtered, washed with three 100 ml portions of water, and dried to give 13.3 g (81%) of veratraldehyde.

EXAMPLE 3

This example illustrates the preparation of 3, 4, 5-trimethoxybenzaldehyde from syringaldehyde.

In an apparatus similar to Example 1, 15.2 g (0.083 mol) of syringaldehyde and 15.0 g (0.11 mol) of potassium carbonate were heated to 105° C. under nitrogen and 15 ml (0.12 mol) of trimethyl phosphate were added over 10 minutes. The mixture was maintained at about 80° C. for 3 hours then cooled to 45° C. and quenched with 50 ml of H₂O. The tan solid which precipitated was collected, washed with 3×50 ml of water and dried to give 15 g (92%) of 3, 4, 5-trimethoxybenzaldehyde.

EXAMPLE 4

This example illustrates the alkylation of p-acetamidophenol to produce p-acetamidoanisole.

To a three-necked 100 ml flask equipped for reflux and fitted with a mechanical stirrer was added 10.0 g (0.066 mol) of p-acetamidophenol, 2.0 g (0.014 mol) of potassium carbonate, and 20 ml (0.17 mol) of trimethyl phosphate. The mixture was heated to 90° C. for three hours then allowed to stand overnight before quenching with 50 ml of water. Extraction into methylene chloride and removal of residual starting material via a base wash with 6% sodium hydroxide solution gave on concentration in vacuo 6.5 g (60%) of p-acetamidoanisole.

EXAMPLE 5

This example illustrates the preparation of salicylaldehyde from o-methoxybenzaldehyde.

To a three-necked 100 ml flask equipped for reflux and fitted with a mechanical stirrer was added 5.0 ml (0.047 mol) of salicylaldehyde, 2.0 g (0.014 mol) of potassium carbonate, and 10.0 ml (0.085 mol) of trimethyl phosphate. The mixture was heated to 85° C. for two hours, then cooled to 50° C. and quenched with 20 ml of water. After two hours the mixture was extracted with 50 ml of methylene chloride, the extracts washed with dilute caustic and then water. The organic extracts were dried over anhydrous potassium carbonate then filtered and concentrated in vacuo to give 3.6 g (53%) of o-methoxybenzaldehyde.

EXAMPLE 6

This example illustrates the preparation of veratric acid methyl ester from vanillic acid.

To a three-necked 100 ml flask equipped for reflux and fitted with a mechanical sitrrer was added 2.0 g (0.012 mol) of vanillic acid, 2.0 g (0.0072 mol) of potassium carbonate, and 10 ml (0.085 mol) of trimethyl phosphate. The mixture was heated to 70° C. for five hours then cooled and quenched with 25 ml of water. The organic portion was extracted into 50 ml of methylene chloride. The extract was washed with dilute sodium hydroxide solution to remove all partially alkylated material and then was washed once with water, dried over anhydrous potassium carbonate, filtered, then concentrated in vacuo to give 1.8 g (77%) of veratric acid methyl ester.

EXAMPLE 7–8

A series of additional reactions were run using melt phase reaction conditions similar to those set forth in the foregoing examples. A slurry of the phenolic substrate was mixed with a half integral quantity of anhydrous potassium carbonate and an integral amount of trimethyl phosphate. This mixture was heated to about 80° C. for three to four hours under a nitrogen atmosphere, cooled, quenched with water, and the product extracted into methylene chloride. Prior to analysis by thin layer chromatography, the methylene chloride extracts were washed with a dilute solution of sodium hydroxide to remove any unreacted phenolic starting material. The ethereal neutral products of reaction were contrasted with the phenolic starting material and a known standard sample of the expected product, where available. Spectral analysis via infrared spectra was used when a question remained as to product identity. The following products were produced from the following starting phenolic compounds:

| Example | Starting Phenol | Product |
|---|---|---|
| 7 | p-acetamidophenol | p-acetamidoanisole |
| 8 | salicylaldehyde | o-methoxybenzaldehyde |

EXAMPLE 9

This example illustrates the preparation of veratraldehyde from vanillin.

In a three-neck flask (capacity 100 ml) equipped with a mechanical stirrer and reflux condenser, 20 ml of dimethylformamide (anhydrous), 5.00 g (0.033 mol) of vanillin and 5.00 g (0.036 mol) of anhydrous potassium carbonate were placed and the mixture was heated under a nitrogen atmosphere to 100° C. The mixture was a clear to amber solution of vanillin with carbonate in suspension. To this mixture was added 5.00 ml (0.043 mol) of trimethyl phosphate over about 5 minutes while maintaining the reaction temperature below 125° C. The mixture was maintained at about 80° C. for one hour and then cooled to 40° C. The mixture was poured into 200 ml water and extracted two times with 50 ml of methylene chloride. The methylene chloride extracts were washed twice with 100 ml of water. The combined extracts were dried over anhydrous potassium carbonate, filtered, and concentrated to give 5.3 g (95%) of veratraldehyde as a pale oil.

EXAMPLE 10

This example illustrates the preparation of 3, 4, 5-trimethoxybenzaldehyde from syringaldehyde.

In an apparatus similar to Example 9, 15.2 g (0.083 mol) of syringaldehyde and 15.0 g (0.11 mol) of potassium carbonate were heated to 105° C. under nitrogen in 50 ml of dimethylformamide and 15 ml (0.12 mol) of trimethyl phosphate were added over 10 minutes. The mixture was maintained at about 100° C. for 3 hours then cooled to 45° C. and quenched with 500 ml of $H_2O$. The quenched reaction was extracted twice with 50 ml of methylene chloride, the combined extracts were washed with 3×50 ml of water and dried over anhydrous $K_2CO_3$. Following filtration and concentration, the product was 15 g (92%) of 3, 4, 5-trimethoxybenzaldehyde.

Trimethyl phosphate was examined for mutagenicity by the Ames test. The Ames test is used to estimate the potential carcinogenicity of chemicals by measuring the number of bacteria which mutate in the presence of the compound being tested relative to the number which spontaneously mutate in the absence of the compound. The Ames test is more fully reported in B. N. Ames, J. McCann, E. Yamasaki, *Mutat. Res.*, 31, 347 (1975). The test results indicated that trimethyl phosphate is on the order of 500 to 1000 times less mutagenic than the alkyl sulfonates which are generally conceded to be orders of magnitude less hazardous than dimethyl sulfate.

From the above, it is apparent that the process of the invention provides a simple but effective route for the preparation of phenolic ethers from phenols with the use of a substantially less hazardous alkylating agent.

We claim:

1. A process for the melt phase preparation of a methylated phenolic ether comprising
    reacting in the absence of a solvent at a temperature of at least the melting point of the phenolic compound a phenolic carbonyl compound containing an unreacted phenolic hydroxy group with trimethyl phosphate until a methylated phenol is produced, said reaction occuring in one step and without the intermediate production of a phenolate.
2. The process of claim 1 in which the phenolic carbonyl compound is a monocyclic phenolic aldehyde.

3. The process of claim 2 in which the phenolic aldehyde is selected from the group consisting of vanillin and syringaldehyde and the alkylated phenol is selected from the group consisting of veratraldehyde and trimethoxybenzaldehyde.

4. The process of claim 1 in which the reaction takes place in the presence of a base catalyst.

5. A process for the preparation of a methylated phenolic ether comprising reacting in the absence of a protic solvent, and in the presence of a dipolar aprotic solvent and a weak base catalyst, a phenolic carbonyl compound containing an unreacted phenolic hydroxy group with trimethyl phosphate until a methylated phenol is produced, said reaction occuring in one step and without the intermediate production of a phenolate.

6. The process of claim 5 in which the solvent is selected from the group consisting of dimethylformamide, dimethylsulfoxide, dimethylacetamide and sulfolane.

7. The process of claim 6 in which the weak base is a carbonate salt selected from the group consisting of sodium, potassium, magnesium and calcium carbonate.

* * * * *